(12) United States Patent
Devens et al.

(10) Patent No.: US 11,857,801 B2
(45) Date of Patent: Jan. 2, 2024

(54) DEVICE FOR TREATMENT OF TRAUMATIC BRAIN INJURY AND RELATED SYSTEMS AND METHODS

(71) Applicant: Regents of the University of Minnesota, Minneapolis, MN (US)

(72) Inventors: Doug Devens, St. Paul, MN (US); Kevin Goodwin, Minneapolis, MN (US); Shannon Smith Williamson, Minneapolis, MN (US); Geoff Daniel, St. Paul, MN (US)

(73) Assignees: REGENTS OF THE UNIVERSITY OF MINNESOTA, Minneapolis, MN (US); AURORA CONCUSSION THERAPY SYSTEMS, Saint Paul, MN (US)

( * ) Notice: Subject to any disclaimer, the term of this patent is extended or adjusted under 35 U.S.C. 154(b) by 311 days.

(21) Appl. No.: 17/050,610

(22) PCT Filed: Apr. 29, 2019

(86) PCT No.: PCT/US2019/029647
§ 371 (c)(1),
(2) Date: Oct. 26, 2020

(87) PCT Pub. No.: WO2019/210304
PCT Pub. Date: Oct. 31, 2019

(65) Prior Publication Data
US 2021/0113853 A1 Apr. 22, 2021

Related U.S. Application Data

(60) Provisional application No. 62/663,400, filed on Apr. 27, 2018.

(51) Int. Cl.
*A61N 5/06* (2006.01)

(52) U.S. Cl.
CPC .... *A61N 5/0622* (2013.01); *A61N 2005/0632* (2013.01); *A61N 2005/0647* (2013.01);
(Continued)

(58) Field of Classification Search
CPC .......... A61N 5/0622; A61N 2005/0632; A61N 2005/0647; A61N 2005/0652;
(Continued)

(56) References Cited

U.S. PATENT DOCUMENTS 6,290,713 B1 * 9/2001 Russell ................ A61N 5/0616
607/91
8,769,723 B1 7/2014 Ilges et al.
(Continued)

FOREIGN PATENT DOCUMENTS

KR 20150007419 A 1/2015
RU 137201 U1 2/2014
(Continued)

OTHER PUBLICATIONS

Potential for Transcranial Laser or LED Therapy to Treat Stroke, Traumatic Brain Injury, and Neurodegenerative Disease Margaret A. Naeser and Michael R. Hamblin Photomedicine and Laser Surgery 2011 29:7, 443-446 (Year: 2011).*

*Primary Examiner* — Brian T Gedeon
*Assistant Examiner* — Joshua Andrew Schum-Houck
(74) *Attorney, Agent, or Firm* — Dentons Davis Brown; Matthew Warner-Blankenship

(57) ABSTRACT

Disclosed herein are various brain injury treatment systems, including various light delivery systems and devices. The various systems include a light delivery device that can be a headpiece or headgear having at least one light array disposed therein and a controller coupled to the at least one light array.

28 Claims, 11 Drawing Sheets

(52) U.S. Cl.
CPC ............... *A61N 2005/0652* (2013.01); *A61N 2005/0659* (2013.01)

(58) Field of Classification Search
CPC .... A61N 2005/0659; A61N 2005/0626; A61B 2090/0803
See application file for complete search history.

(56) References Cited

U.S. PATENT DOCUMENTS

| | | | |
|---|---|---|---|
| 2006/0167532 A1 | 7/2006 | Parker | |
| 2006/0253177 A1* | 11/2006 | Taboada | A61N 5/0613 607/88 |
| 2007/0208395 A1* | 9/2007 | Leclerc | A61N 5/0616 607/86 |
| 2010/0106077 A1* | 4/2010 | Rabin | A61N 5/0617 604/20 |
| 2010/0204762 A1* | 8/2010 | De Taboada | A61N 5/0613 607/88 |
| 2011/0015707 A1 | 1/2011 | Tucker et al. | |
| 2011/0092863 A1 | 4/2011 | Kim et al. | |
| 2013/0058080 A1 | 3/2013 | Ge et al. | |
| 2013/0066404 A1 | 3/2013 | Tapper et al. | |
| 2015/0297914 A1* | 10/2015 | Hamid | A61N 5/0617 607/89 |
| 2015/0375007 A1* | 12/2015 | Takeuchi | A61N 5/0617 607/90 |
| 2016/0067087 A1* | 3/2016 | Tedford | A61N 5/0624 606/4 |
| 2016/0235980 A1 | 8/2016 | Berman et al. | |
| 2017/0028216 A1* | 2/2017 | Medendorp, Jr. | A61N 5/0616 |
| 2017/0165485 A1 | 6/2017 | Sullivan et al. | |

FOREIGN PATENT DOCUMENTS

| | | |
|---|---|---|
| WO | 2005025672 A1 | 3/2005 |
| WO | 2007047892 A1 | 4/2007 |
| WO | 2007073106 A1 | 6/2007 |
| WO | 2008144157 A1 | 11/2008 |

\* cited by examiner

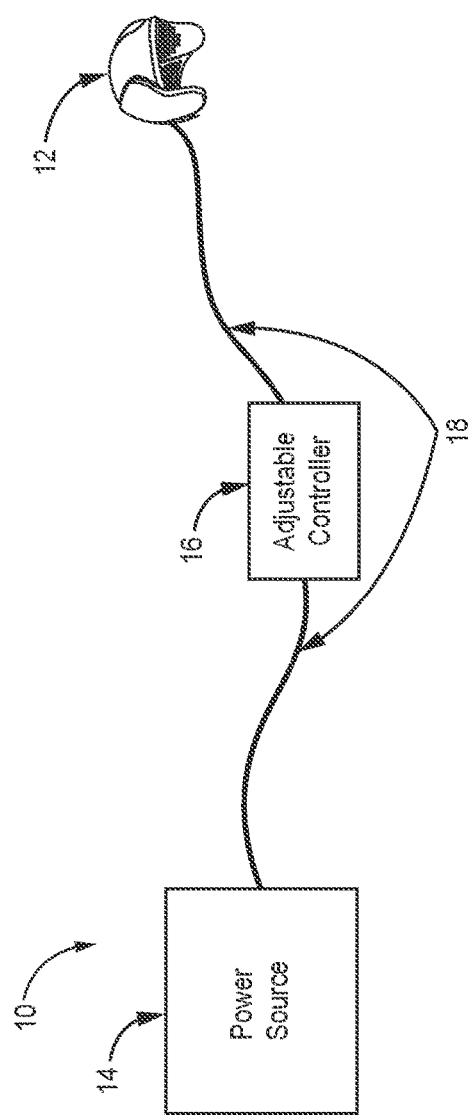
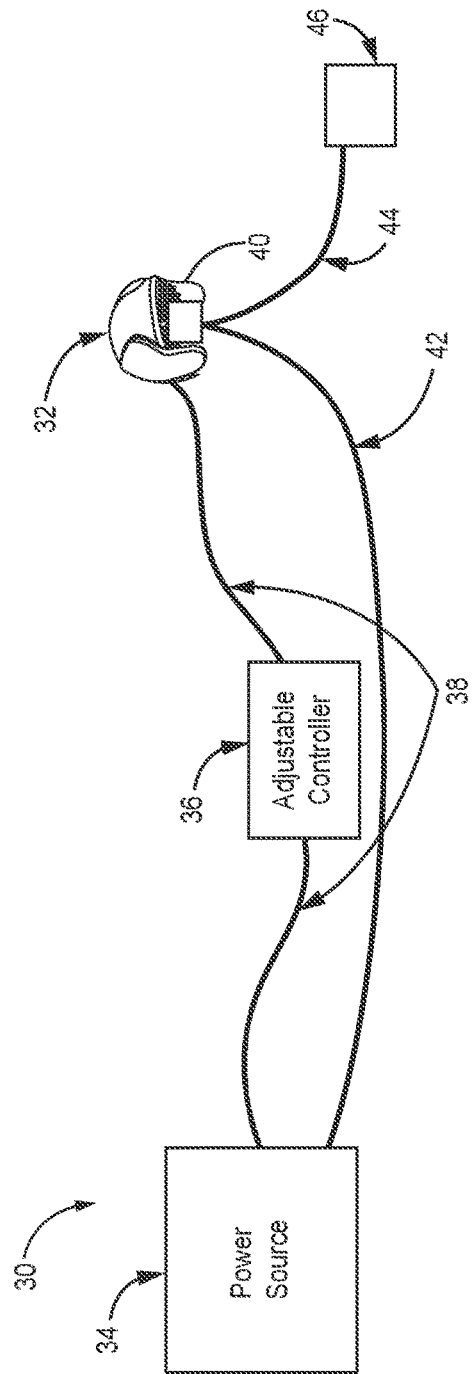

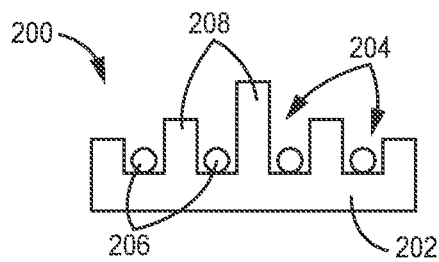
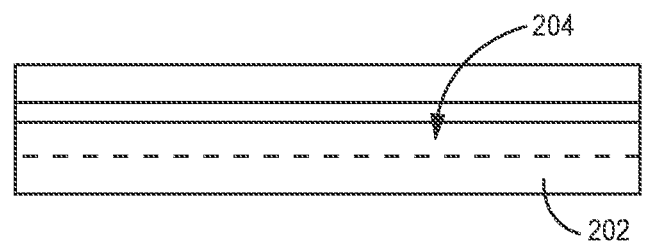
FIG. 11A  FIG. 11B
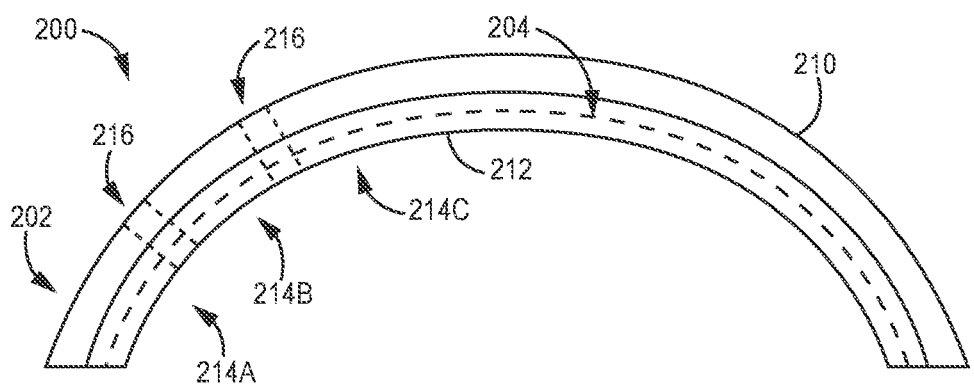
FIG. 11C
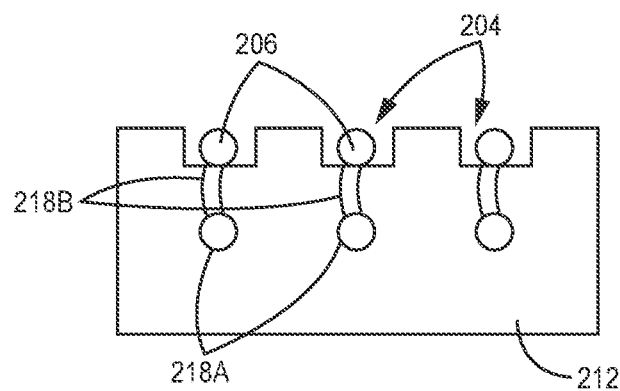
FIG. 11D

DEVICE FOR TREATMENT OF TRAUMATIC BRAIN INJURY AND RELATED SYSTEMS AND METHODS

CROSS-REFERENCE TO RELATED APPLICATION(S)

This application claims priority to International PCT Application No. PCT/US19/29647, filed on Apr. 29, 2019 and entitled "Device for Treatment of Traumatic Brain Injury and Related Systems and Methods", which claims priority to U.S. Provisional Application 62/663,400, filed Apr. 27, 2018 and entitled "Device for Treatment of Traumatic Brain Injury and Related Systems and Methods," which is hereby incorporated herein by reference in its entirety.

FIELD OF THE INVENTION

The various embodiments herein relate to neural treatment technologies, including treatment for traumatic brain injury such as concussion.

BACKGROUND OF THE INVENTION

Traumatic brain injury ("TBI") affects approximately 1.5 to 8 million people in the United States each year with approximately 75% to 90% classified as a mild TBI—also known as a concussion. TBI is a disruption in the normal function of the brain that can be caused by an impact or a penetrating head injury. The acceleration-deceleration forces transmitted by the trauma cause a cascade of neurochemical and neurometabolic events producing this brain dysfunction. At the cellular level, diffuse stretching of the neuronal and axonal membranes initiates the release of neurotransmitters and unregulated ion movement across axonal membranes. This ionic derangement leads to mitochondrial calcium overloading causing organelle malfunction. Specifically, this calcium burden uncouples the oxidative phosphorylation needed for adenosine tri-phosphate (ATP) formation simultaneously decreasing energy production capacity and increasing reactive oxygen species accumulation within neurons. Coincidentally, this increased oxidative stress only further inhibits the damaged mitochondria ATP-production. However, in order to re-establish the pre-traumatic ionic balance necessary for nerve signal transmission, cells require additional ATP to power the ionic pumps and maintain homeostasis. Neurons are therefore in an energy crisis with increased energy demand and decreased ATP production. The neurons do compensate slightly by shifting to a less efficient form of oxygen independent glycolysis. However, this is insufficient to match the cellular requirements to function properly.

This impaired brain function caused by a TBI can subsequently present with a variety of symptoms including, but not limited to, altered consciousness, emotional lability, memory loss, neurologic deficits, sleep disturbances, balance deficiency and cognitive impairment. Currently, based on the clinical severity and duration of symptoms—plus the characteristics and location of the injury—patients are classified as either mild, moderate or severe.

Treatment modalities currently focus on symptom management primarily through cognitive rest, activity reintegration and different types of psychosocial and physical therapy. While 80-90% of patients who are properly diagnosed have been found to respond to therapy over approximately 2-3 weeks, there still remains a major concern regarding how the injury can affect long-term quality of life.

Due to the limited number of treatment options, there is a large interest in developing new and improved therapies for TBI. Research is currently being conducted evaluating different combinations of physical therapy, medications, and a variety of non-invasive devices including compression vests, neurovision rehab and direct current stimulation. However, none of these options have yet to prove clinical significance.

There is a need in the art for an improved treatment for traumatic brain injury that improves the quality and speed of recovery.

BRIEF SUMMARY OF THE INVENTION

Discussed herein are various brain injury treatment systems, including various light delivery systems and devices.

In Example 1, a traumatic brain injury treatment system comprises a headpiece comprising a housing comprising a head cavity and a light array disposed on an inner surface of the head cavity. The system further comprises a controller operably coupled to the light array via a first connection line and an energy source operably coupled to the controller via a second connection line.

In Example 1, a traumatic brain injury treatment system comprises a headpiece comprising a housing and a light array. The housing comprises a head cavity defined by the housing, and an inner surface within the head cavity. The light array is disposed on the inner surface, wherein the light array comprises a plurality of LED light assemblies. Further, the system also comprises a power/communication line coupled to the light array, a controller coupled to the power/communication line, and an energy source coupled to the power/communication line.

Example 3 relates to the traumatic brain injury treatment system according to Example 2, wherein each of the plurality of LED light assemblies comprises a substantially transparent tubular structure, an LED light disposed at a fixed longitudinal position with the tubular structure, and a tension component coupled to the tubular structure and the inner surface of the housing.

Example 4 relates to the traumatic brain injury treatment system according to Example 3, wherein each of the plurality of LED light assemblies further comprises a cover disposed on a proximal end of the tubular structure, wherein the tension component is coupled to the tubular structure at the cover.

Example 5 relates to the traumatic brain injury treatment system according to Example 3, wherein the tension component comprises at least one spring.

Example 6 relates to the traumatic brain injury treatment system according to Example 3, wherein the tension component comprises a lever.

Example 7 relates to the traumatic brain injury treatment system according to Example 3, wherein the tubular structure is disposed through an opening in the inner surface of the housing.

Example 8 relates to the traumatic brain injury treatment system according to Example 3, wherein the tubular structure is disposed adjacent to and tensionably coupled to the inner surface.

Example 9 relates to the traumatic brain injury treatment system according to Example 3, wherein the tubular structure is disposed at least partially within a cavity defined within the inner surface.

Example 10 relates to the traumatic brain injury treatment system according to Example 2, wherein the housing further comprises two movable side panels hingedly coupled to the housing, wherein the two movable side panels comprise a closed position and an open position.

Example 11 relates to the traumatic brain injury treatment system according to Example 2, wherein the housing further comprises a movable rear panel hingedly coupled to the housing, wherein the movable rear panel comprises a closed position and an open position.

Example 12 relates to the traumatic brain injury treatment system according to Example 2, wherein the housing comprises a substantially flexible material.

Example 13 relates to the traumatic brain injury treatment system according to Example 2, wherein the housing comprises a substantially rigid material.

Example 14 relates to the traumatic brain injury treatment system according to Example 2, wherein the housing further comprises a visor disposed on a front portion of the housing.

Example 15 relates to the traumatic brain injury treatment system according to Example 2, wherein the housing further comprises two ear coverings, wherein each of the two ear coverings is disposed on a side of the housing.

Example 16 relates to the traumatic brain injury treatment system according to Example 2, wherein the plurality of LED light assemblies further comprise a portion of the LED light assemblies disposed adjacent to a front sinus or a mastoid process of a patient's head when the patient's head is disposed within the housing, wherein the portion of the LED light assemblies disposed adjacent to the front sinus or the mastoid process have a greater radiant intensity or are actuated to radiate for a longer period of time than other LED light assemblies in the plurality of LED light assemblies.

Example 17 relates to the traumatic brain injury treatment system according to Example 16, wherein the greater radiant intensity ranges from about 15% to about 50% greater intensity than the other LED light assemblies in the plurality of LED light assemblies.

Example 18 relates to the traumatic brain injury treatment system according to Example 16, wherein the greater radiant intensity results from a more powerful LED light or a shorter distance between an LED light and an irradiated surface of the patient's head.

Example 19 relates to the traumatic brain injury treatment system according to Example 2, wherein the plurality of LED light assemblies further comprise a portion of the LED light assemblies disposed adjacent to a sphenoid bone of a patient's head when the patient's head is disposed within the housing, wherein the portion of the LED light assemblies disposed adjacent to the sphenoid bone have a lesser radiant intensity than other LED light assemblies in the plurality of LED light assemblies.

Example 20 relates to the traumatic brain injury treatment system according to Example 19, wherein the lesser radiant intensity results from a less powerful LED light or a greater distance between an LED light and an irradiated surface of the patient's head.

Example 21 relates to the traumatic brain injury treatment system according to Example 2, wherein specific portions of the plurality of LED light assemblies have predetermined, differing radiant intensities depending on a position of the specific portions within the housing.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

BRIEF DESCRIPTION OF THE DRAWINGS

FIG. 1 is a schematic depiction of a light delivery system, according to one embodiment.

FIG. 2 is a schematic depiction of a light delivery system, according to another embodiment.

FIG. 11A is a cross-sectional side view of a headgear wall with conductor channels, according to one embodiment.

FIG. 11B is a side view of the headgear wall of FIG. 11A.

FIG. 11C is a cross-sectional side view of a headgear wall with three light array sections, according to one embodiment.

FIG. 11D is a cross-sectional side view of a conductor layer, according to one embodiment.

DETAILED DESCRIPTION

Figure 3:
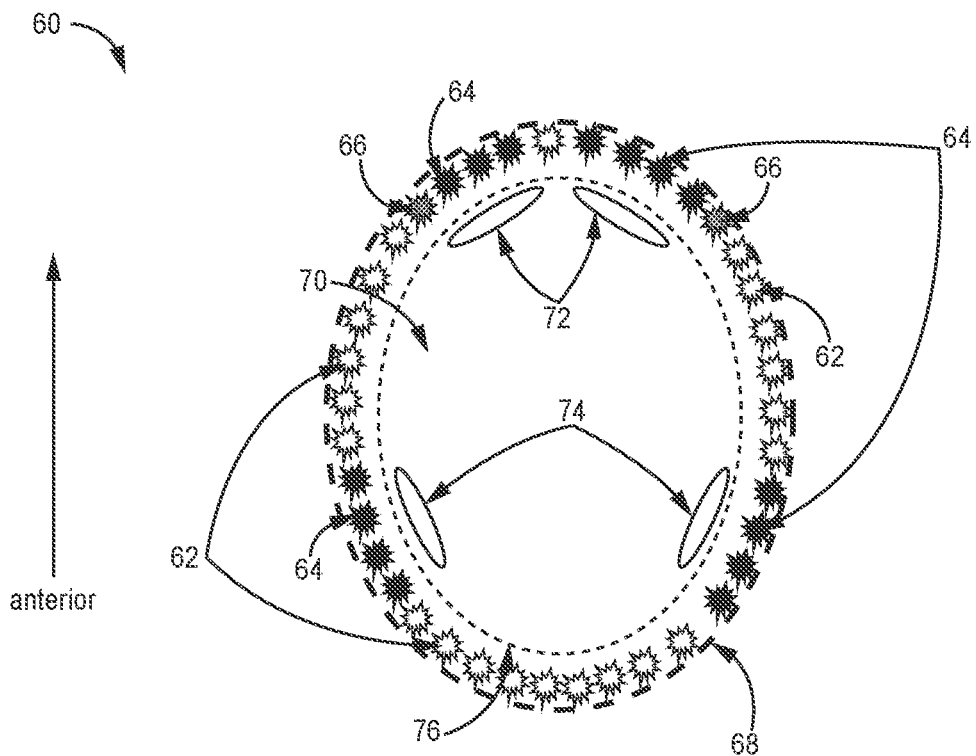
FIG. 3 is a cross-sectional depiction of a light delivery device, according to one embodiment.

The various embodiments disclosed or contemplated herein relate to devices and systems for delivering near infrared light to the head and brain of concussion victims.

As shown in FIG. 1, the system 10 according to one embodiment has a light delivery device 12, a power source 14, and a controller 16. These three components are coupled to each other as shown via a power/communication line 18. More specifically, the power/communication line 18 couples the power source 14 to the controller 16, and the line 18 further couples the controller 16 to the light delivery device 12. Alternatively, the power/communication line 18 can constitute two separate lines, with one coupling the power source to the controller 16 and the other coupling the controller 16 to the light delivery device 12. According to one embodiment, the power/communication line 18 is a cable 18. Alternatively, the power/communication line 18 can be any known elongate line for transmitting both energy and electronic communication.

In this embodiment, the controller 16 can be adjusted variably to deliver the required amount of power, and can be set to a timer to allow the power to be reduced or eliminated after a set, desired amount of time. The modulated power from the controller 16 is delivered to light delivery device 12 that is typically positioned on a patient's head. In one embodiment, the controller 16 is a rheostat 16. Alternatively, the controller 16 can be any type of processor or computer 16 that can be used to control the various components of the system 10 and can have software (or have access to software) that can provide various processes and/or applications that provide additional control features to the controller 16. The device 12 has LED lights (not shown) that convert the energy into therapeutic near infrared radiation, as will be described in additional detail below. The electronic circuits within the device 12 for powering and controlling the LEDs (not shown) are not shown here but are apparent to one of ordinary skill in the art.

According to one embodiment, the energy source 14 is line voltage available via an outlet. Alternatively, the energy source 14 is a battery (or batteries). In a further alternative, the energy source 14 can be any known energy source for providing energy to a system such as described herein.

The light delivery device 12, in accordance with the specific implementation as shown in FIG. 1, is a helmet 12 that is disposed on the patient's head. Alternatively, the light delivery device 12 is a flexible headcover. Specific embodiments of these types of light delivery devices will be described in further detail below. In a further alternative, the light delivery device 12 can be any known device that can be disposed on or over the patient's head (also referred to as "headgear," a "headpiece," and a "head covering") and can contain the array of lights according to the various embodiments herein such that light treatment can be applied to the patient's head. The lights, according to one implementation, are LED lights. Various other embodiments discussed herein include LED lights. Alternatively, the lights in any of the various implementations disclosed or contemplated herein can be any known type of lights for use in a device for irradiating a patient in a fashion similar to the various device embodiments herein. It is understood that any of these various types of light delivery devices described herein can be incorporated into any of the embodiments disclosed or contemplated elsewhere herein.

FIG. 2 shows another embodiment of a therapeutic system 30. In this implementation, in addition to the light delivery device 32, the power source 34, and the controller 36 coupled to each other as shown via a power/communication line 38, the system 30 also has a light measurement device 40 such as, for example, a spectrometer 40, that is disposed within the light delivery device 32 and positioned against or otherwise in contact with or adjacent to the patient's scalp. It is understood that the components (such as the light delivery device 32, the power source, the controller 36, and the power/communication line 38) in this embodiment having equivalent components in the system 10 described above are substantially similar to those equivalent components in the system 10 as described above.

The light measurement device 40, which is, in this example, a near infrared spectrometer 40, mentioned above is disposed within the headgear 32 to measure the irradiance delivered at the skin of the patient by the light array (not shown) in the headgear 32. In one implementation, the spectrometer 40 is coupled to an energy/communication line 42 that can transfer energy and/or communication therein. According to one embodiment, the output from the spectrometer 40 can be (1) transmitted by a signal output cable 44 to a processor 46 that can convert the output to human-readable form (via, for example, an interface or display on the processor 46, for example), or (2) transmitted to a microprocessor within the controller 36 to modulate the output of the controller 36 to maintain a desired irradiance at the wearer's scalp by the LED light array (not shown) in the headgear 32. The control algorithm to modulate the output of the controller 36 in response to data from the spectrometer 40 is not shown here but would be apparent to one of ordinary skill in the art.

Figure 4:
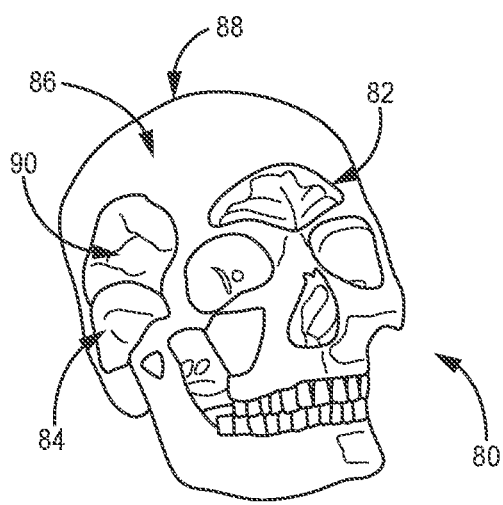
FIG. 4 is a perspective view of a human skull.

FIG. 3 shows a cross-sectional top view of one embodiment of the therapeutic headgear 60, with FIG. 4 depicting one example of the skull 80 of a patient on which the headgear 60 might be positioned. The headgear 60 has an array of lights 62, 64, 66 disposed on the inner surface of the wall 68 of the headgear 60 to deliver near infrared radiation to the patient's head 70. The lights 62, 64, 66 are selected to ensure uniform radiation around the entire head 70. According to one implementation, the lights 62, 64, 66 are LED lights of specific intensities that are selected to ensure uniform radiation around the patient's head 70. For example, in this specific embodiment, over the front sinuses 72 and mastoid processes 74 inside the cranium wall 76, the lights are LED lights 64 that are selected to have anywhere between 15% and 50% more power or radiant intensity than LED lights 62. Similarly, LED lights 66 over the sphenoid bones 86 (as best shown in the exemplary skull in FIG. 4) have less power than the LED lights 62.

FIG. 4, as mentioned above, shows an exemplary human skull 80 provided herein to show specific anatomic details relevant to various aspects of certain embodiments. Of particular note are the frontal sinuses 82 and the mastoid processes 84. These features are air pockets 82, 84 within the skull 80 in which there is a transition from bone, to air, to bone again. These transitions between media with different refractive indices can cause of transmission loss of incident radiation due to scattering, reducing radiation transmission to the brain. Similarly, the lateral part of the frontal skull 86, the posterior parietal region of the parietal skull 88 and the sphenoid bone 90 are all regions where the bone is especially thick 86, 88 or particularly thin 90. To ensure that incident radiation is uniform at the surface of the brain (after it passes through the skull 80), certain treatment device embodiments herein are configured as described to compensate for these variations in transmissibility of the skull 80 to incident radiation.

In any of the various implementations set forth herein, including the systems embodiments 10 and 30 set forth in FIGS. 1 and 2 and discussed above and any of the other systems and devices (including the various headgear and light assembly embodiments discussed in detail below) disclosed or contemplated herein, the application of the light to the patient's head (such as the head 70 discussed above, for example) can be varied based on intensity or duration of the light. That is, the fluence can be varied to achieve the desired output of each light in any system embodiment disclosed or contemplated herein.

"Fluence" is the total output of a light source and is calculated as irradiance multiplied by the time it is applied. In the various systems and devices herein, fluence of any light or group of lights can be modulated by either changing the level of irradiance or the period of time over which the irradiance is applied. Thus, to increase fluence applied to a given part of the scalp by one or more lights, one may increase the time during which the irradiance is applied by that one or more lights. Fluence increases linearly with increase in time, while irradiance remains constant.

According to the various embodiments herein, the amount of fluence of a light or array of lights of any device disclosed or contemplated herein that penetrates to the cortex of the patient (referred to herein as "therapeutic fluence") is a function of the amount of fluence that is applied to the scalp (referred to herein as "applied fluence") and an inverse function of the patient's cranial thickness. As discussed elsewhere herein, cranial thickness varies between patients, thereby resulting in variations in the amount of light penetration through those patients' skulls. As a result, according to various implementations herein, the various systems and devices disclosed or contemplated herein can provide for tailoring the light therapy to each individual patient by adjusting the applied fluence based on measurements of the patient's skull to control the amount of therapeutic fluence delivered to that patient's brain.

One exemplary method of using the various system and device embodiments herein to provide tailored light application to a patient's brain is provided as follows. In this exemplary implementation, after diagnosis of a concussion in the patient, the physician then performs (or accesses from a previous, unrelated exam) measurements of the patient's cranium to determine its thickness. Measurement methods include any known method for measuring a patient's cranium, including, for example, use of ultrasound with the transducer applied to the scalp at one or various positions around the head, use of a computerized tomograph which allows measurement of cranial thickness simultaneously at multiple positions on the head, and use of magnetic resonance imaging, which also allows for simultaneous cranial thickness measurement at multiple positions around the head.

Once the patient's cranial thickness measurements are collected, those measurements can be used according to various embodiments of the devices or systems herein to tailor the level of applied fluence in order to arrive at the desired level of therapeutic fluence for the patient. More specifically, the applied fluence can be adjusted based on a reference irradiance and time for a reference cranial thickness. In certain embodiments, the adjustment is carried out by the physician adjusting physical controls (power and timing) on the system/device based on consultation with the reference thickness and reference therapeutic fluence level, which can be provided to the physician in a hardcopy manual, an electronic manual, an electronic app, or any other format or medium. Alternatively, any of the system or device embodiments herein can have software that contains the reference cranial thickness and reference therapeutic fluence level such that the software provides for automatic adjustment of the applied fluence based on the reference information to arrive at the correct level of therapeutic fluence.

More specifically, in those implementations in which the physician manually adjusts the system/device, the physician can adjust either the irradiance or time of light application by the device/system to increase the applied fluence delivered if the patient's cranial thickness is greater than the reference value, or to decrease the irradiance or time of light application to decrease the applied fluence if the patient's cranial thickness is smaller than the reference value. The increase or decrease of the therapy irradiance or time compared to the reference values would be proportional to the relative increase or decrease of the patient's cranial thickness compared to the reference cranial thickness. In certain implementations, the adjustment of the applied fluence can be done as an average for the entire cranium or, alternatively, the adjustment can be done by zones of lights disposed adjacent to target zones of the patient's head, including, for example, the frontal sinus, frontal, parietal, crown, occipital, mastoid, and temporal zones.

In accordance with those embodiments in which any of the device or system embodiments herein includes software that utilizes reference cranial thicknesses and corresponding reference therapeutic fluence levels, the physician can, in certain of those embodiments, enter the cranial measurements into the computer interface and the software automatically compares the entered cranial thickness measurements against reference values and increase or decrease the irradiance or time compared to the reference values to increase or decrease the applied fluence in proportion to the increase or decrease of the patient's cranial thickness with respect to the reference values. According to certain implementations, the software can provide options for the physician to choose either adjustment in power, time of therapy, or both. As such, the software would allow for the device/system to adjust the applied fluence delivered to multiple zones around the head, thereby tailoring the therapy to the patient.

Figure 5:
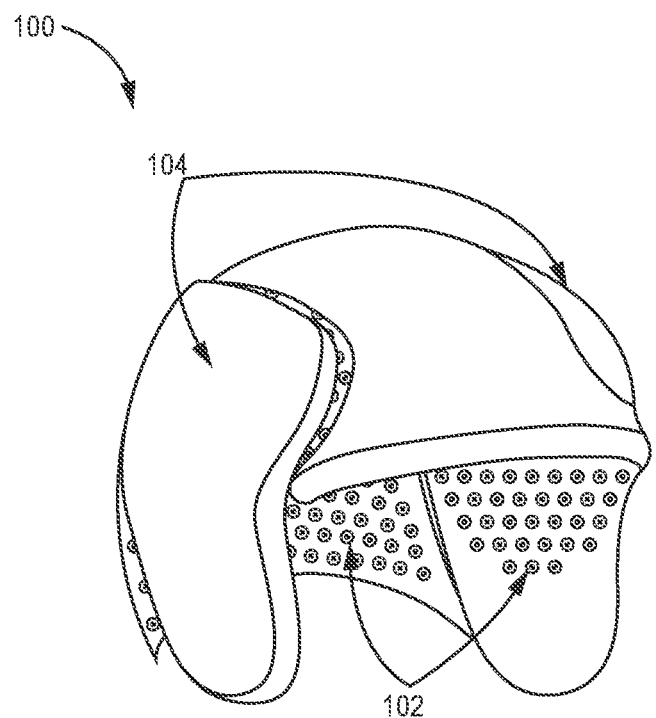
FIG. 5 is a perspective view of a light delivery device, according to one embodiment.
Figure 6:
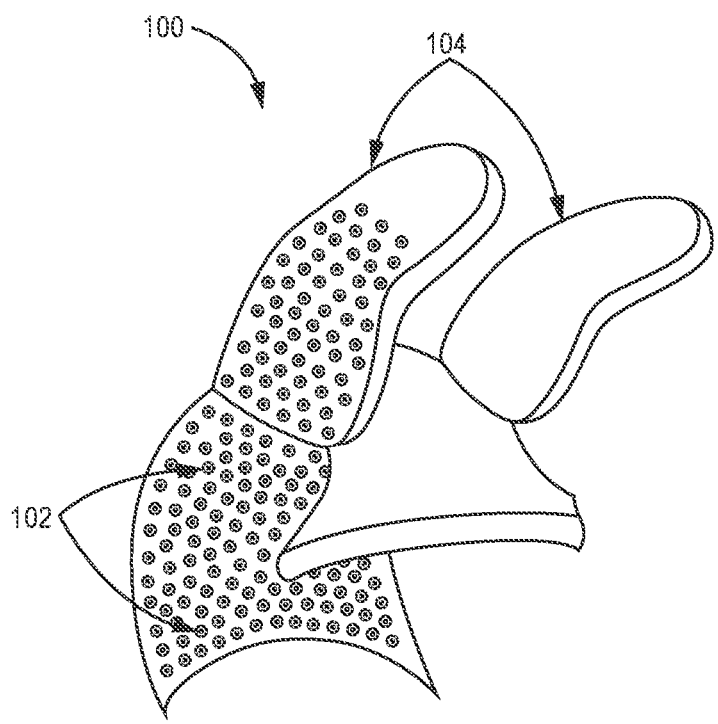
FIG. 6 is a perspective view of the light delivery device of FIG. 5 with the side panels deployed, according to one embodiment.

FIGS. 5 and 6 show one embodiment of a light delivery device 100, which in this specific implementation is a therapeutic headgear 100. The headgear 100 fits around the concussion victim's head and is, in one implementation, attached to a controller (such as, for example, one of the controllers 16, 36 discussed above) via an energy/communication line (such as, for example, the lines 18, 38 described above). It is understood that the headgear 100 can be incorporated into any of the system embodiments disclosed or contemplated herein, and can incorporate any of the features and/or components of any of the embodiments disclosed or contemplated herein. The headgear 100 can have a material (such as a known foam or other known material used for the interior of a motorcycle helmet or other similar headgear) disposed on the inner wall or surface of the headgear 100 that can be shaped and structured to form to a user's head. Further, the therapeutic headgear 100 has an LED light array 102 disposed or otherwise arranged on the inner surface or wall of the headgear 100. In one implementation, the lights of the light array 102 are arranged in a configuration similar to the LED lights 62, 64, 66 in FIG. 3, with higher and lower intensity LED lights 62, 64, 66 as described above.

In accordance with certain exemplary embodiments, including the headgear 100, to make donning the headgear 100 (or otherwise positioning the headgear 100 over a patient's head) simpler, the headgear 100 has movable, hinged gullwings (or "panels") 104 that move between a closed position and an open position. The closed position, according to one implementation, is depicted FIG. 5. FIG. 6, in contrast, depicts the gull wing panels 104 in the open position for donning before use. There is also an array of LED lights 102 distributed on the inner surface or wall of the gullwing panels 104 in this implementation. As discussed above, this array 102 can be arranged as disclosed with respect to FIG. 3. In use, the panels 104 can be placed in their open position or configuration prior to positioning the headgear 100 on the patient's head. Once the headgear 100 is positioned as desired, the panels 104 can be moved into their closed position or configuration prior to treatment. Alternatively, the light delivery device 100, and any similar device herein, can have no moveable panels.

Figure 7:
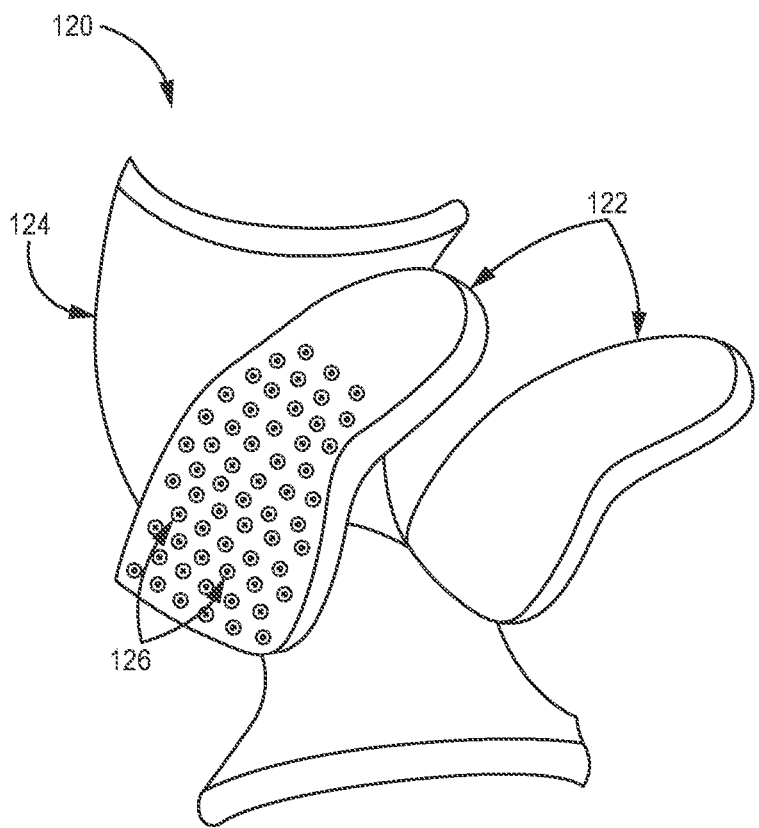
FIG. 7 is a perspective view of a light delivery device, according to another embodiment.

FIG. 7 shows another embodiment of a light delivery device 120 that is a therapeutic headgear 120. In this embodiment, in addition to the moveable side panels 122 that operate in substantially the same way and have substantially the same features as the panels 104 discussed above, the headgear 120 has a moveable, hinged rear gullwing panel 124. Like the side panels 122, the rear panel 124 has an array of LED lights 126 distributed on the inner surface or wall thereof in this implementation. As discussed above, this array 126 can be arranged as disclosed with respect to FIG. 3. Further, like the headgear 100, the headgear 120 has an LED light array 126 disposed or otherwise arranged on the inner surface or wall of the headgear 120, which can also be arranged in a fashion similar to the configuration of FIG. 3. The rear panel 124 is moveable between a closed position (not shown) and an open position as shown in FIG. 7. In one exemplary implementation, the moveable rear panel 124 further simplifies or provides even greater ease in donning the headgear 120 or otherwise positioning the headgear 120 on a patient's head. In use, the side panels 122 and the rear panel 124 can be placed in their open positions or configurations prior to positioning the headgear 120 on the patient's head. Once the headgear 120 is positioned as desired, the panels 122, 124 can be moved into their closed position or configuration prior to treatment.

Figure 8:
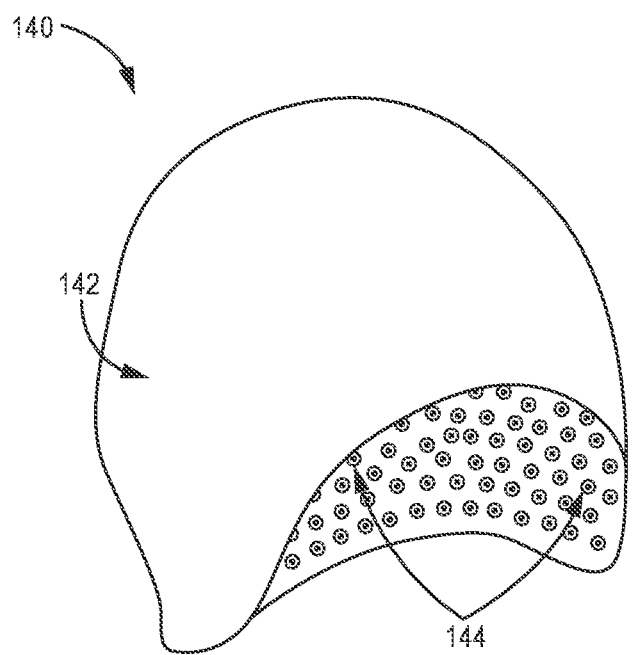
FIG. 8 is a perspective view of a light delivery device, according to a further embodiment.

FIG. 8 shows yet another embodiment of a light delivery device 140 that is a therapeutic headgear 140. In this embodiment, the wall or body material 142 of the headgear is an elastic, stretchable material that can be stretched to fit over the user's head. For example, in one embodiment, the headgear 140 fits over the patient's head in a fashion similar to a snugly fitting stocking cap or other such head covering. The material can be any known stretchable material that can be incorporated into headgear such as this. Further, like the headgear 100, 120, the headgear 140 has an LED light array 144 disposed or otherwise arranged on the inner surface or wall of the headgear 140, which can also, in certain embodiments, be arranged in a fashion similar to the configuration of FIG. 3.

Figure 9:
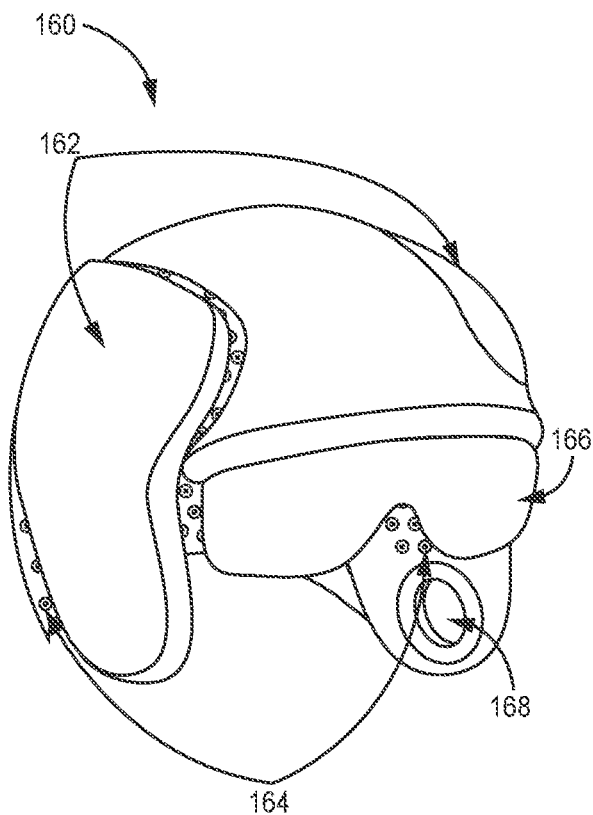
FIG. 9 is a perspective view of a light delivery device, according to yet another embodiment.

FIG. 9 depicts a further implementation of a light delivery device 160 that is a therapeutic headgear 160. This headgear embodiment 160 has movable, hinged lateral gullwing panels 162 substantially similar to the side panels 104, 122 discussed above. Further, like the headgear 100, 120, 140, the headgear 160 has an LED light array 164 disposed or otherwise arranged on the inner surface or wall of the headgear 160 (including the panels 162), which can also, in certain embodiments, be arranged in a fashion similar to the configuration of FIG. 3. In this specific embodiment, the headgear 160 also has a visor 166 disposed on front portion of the headgear 160 that will generally be positioned in front of the eyes of the patient when the headgear 160 is disposed on the patient's head. As such, the visor 166 can block or reduce the external or ambient light reaching the patient's eyes. In one embodiment, the visor 166 is substantially opaque and allows essentially no light to the patient's eyes. Further, the headgear 160 in this specific implementation has ear covers 168 disposed on a lower portion of the panels 162 such that the covers 168 are positioned adjacent to (and typically in contact with) the patient's ears, thereby reducing or blocking any external or ambient sound from reaching the patient's ears. It is understood that the visor and/or the ear covers can be incorporated into any of the headgear embodiments disclosed or contemplated herein.

It is understood that the various headgear device embodiments disclosed above (including headgears 100, 120, 140, 160) or contemplated herein can be incorporated into any system as disclosed or contemplated herein, including either of systems 10, 30 described above. Further, it is understood that the various headgear implementations herein can be operated as described in detail above to tailor the applied fluence to each specific patient to achieve the desired therapeutic fluence via manual adjustments or software. In certain of those embodiments, any of the headgear embodiments herein can have two or more zones of light assemblies that are adjacent to certain zones of the patient's skull, thereby providing for variation in applied fluence between those zones based on physical differences between the skull zones. That is, each of the two or more light assembly zones can be operable separate from the other light assembly zones, thereby allowing for the each zone to be controlled separately with respect to both intensity and duration. In certain specific implementations, there are specific lighting assembly zones that correspond to each of the specific skull zones having different physical characteristics that impact how much light can pass through each of those skull zones.

As such, the two or more lighting assembly zones in any headgear embodiment herein allow for control of the duration and/or intensity of the irradiance generated by each of those zones. In certain implementations, the adjustment of the irradiance is made via either (1) manual control in the form of a physical on/off switch (or any other known type of manual control) coupled with each light assembly zone or (2) automated control in the form of either hardware logic or software controlling activation or deactivation of the power to the various light array zones. One exemplary embodiment of automated control via a hardware logic controller is a system having an Arduino Uno™, which is commercially available from Arduino (www.arduino.cc), as the logic controller that is programmed for this control. In those implementations in which a logic controller is used, the system would allow for the physician (or other user) to adjust a control (such as a knob, button, or any other known control) to set the duration and/or intensity for each zone. Alternatively, in those system embodiments having a controller with software, the system would provide for an interface into which the physician (or other user) would be able input the patient's specific cranial measurements and also select the irradiance variable to be adjusted (either duration or intensity). The software would then automatically calculate the appropriate time or intensity for each light assembly zone required by the cranial measurements to achieve the appropriate therapeutic fluence. In either type of system (hardware or software), the controller then controls the application of irradiance individually for each light assembly zone, per control of the relays, so that proper fluence is delivered as determined by the skull thickness measurement and correlated therapy time or intensity. When the elapsed time for a zone is equal to the required time, or the irradiance intensity for that zone is equal to the required intensity, and thus proper fluence is achieved, the controller will trigger the relay to the off mode so that power is shut off for that zone and the therapy delivery is ended.

Figure 10:
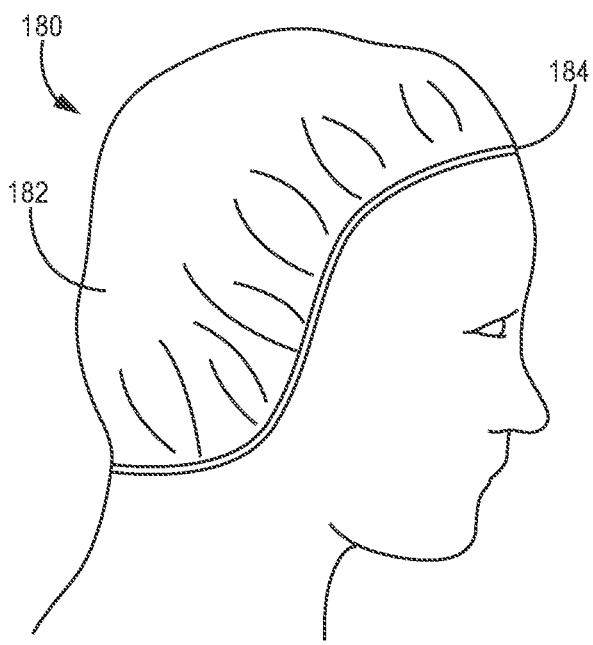
FIG. 10 is a side view of a protective cap, according to one embodiment.

In certain implementations, the various system and headgear embodiments disclosed or contemplated herein can be utilized in a hospital or clinic setting such that the headgear is used repeatedly by different patients. As best shown in FIG. 10, one approach to help maintain the cleanliness and hygiene of the interior of the headgear is to provide a cap 180 for the patient to place on the patient's head prior to donning the headgear device. This cap 180, according to this embodiment, can have a cap body 182 and an elastic band 184 disposed around the cap body to help secure the cap 180 to the patient in a fashion and form similar to a shower cap. In one implementation, the cap body 182 is made of polyethylene terephthalate copolymer ("PETG"), which has a very low absorbance of near infrared wavelengths. The cap 180 with the PETG body can prevent the headgear device from becoming soiled but also allow maximal transmission of therapeutic energy. Alternatively, the cap 180 can have a cinchable cord or can take any other known cap form. In a further alternative, the cap body 182 can be made of any material that has a low absorbance of near infrared wavelengths, thereby allowing for maximum transmission of the therapeutic energy.

According to one embodiment, any of the headgear embodiments disclosed or contemplated herein can have the following internal electrical arrangement and connections in order to ensure delivery of electrical power to all of the light assemblies in the light array within the headgear. According to this implementation, the headgear can have a central large-amperage supply line and a large-amperage neutral/ground line both extending along a middle portion of the headgear. Further, the arrangement has relatively smaller wires that extend from the central supply line to the individual light arrays and return to the large neutral line. In certain embodiments, the relatively smaller wires are thinner and more flexible and have a lower amperage than the central supply line. This arrangement reduces the amount of wire supplying the light arrays and thus reduces the space requirements in the headgear or light delivery device, thereby reducing the size requirements thereof.

As shown in FIGS. 11A-11C, according to one implementation, the internal electrical arrangement 200 is a flexible machined, extruded, or 3D printed structure 200 with two or more channels running the length of the light delivery device. More specifically, as best shown in FIGS. 11A and 11B, the specific exemplary embodiment depicted has four channels 204 formed in the headgear wall 202, with an elongate conductor 206 disposed in each channel 204. The elongate conductors 206 are flexible, or malleable, elongate wires or foils made of conductive material (such as, for example, copper) to carry current from the central supply line to the light assemblies and/or the light sections (as discussed elsewhere herein). The channel walls 208 separate each channel 204, thereby electrically isolating the conductors 206. In one embodiment, each conductor 206 can carry enough power for the light array zone or section it is intended to power, or enough power for the return to the neutral/ground line. In one exemplary implementation, the amperage level for the power delivery conductors 206 will be up to 20 amps, while the neutral/ground conductors 206 will be able to carry up to 40 amps. In certain embodiments, the channels 204 can have screws or other attachment devices (not shown) disposed through the conductors and into the polymer base of the headgear wall 202 for easy attachment of the wires (not shown) from the light assemblies or arrays thereof. Alternatively, it is understood that spring contacts and solder joints or any other known attachment mechanisms are also potential designs for attachment of the wires.

According to various implementations, the number of conductors 206 (and thus channels 204) can vary according to the configuration of the electrical arrangement 200 and the number of light array sections in the headgear wall 202. For example, in one implementation, the arrangement 200 can have up to nine conductors, with eight of the conductors being power circuits and one of the conductors being a ground. Alternatively, the arrangement 200 can have any number of conductors.

In certain embodiments, the thickness and/or the height of the walls 208 can depend on the amount of power being transmitted through the conductors 206. For example, in various implementations, the ground conductor 206 can be carrying a lot more power than the power conductors 206, and thus the walls 208 surrounding the channel 204 containing the ground conductor 206 can be thicker and/or taller than the walls 208 surrounding the other channels 204. The heights of the walls 208 are shown at different heights to reflect this possibility.

In accordance with the embodiment of FIG. 11C, the headgear wall 202 has an outer layer (or "cover layer") 210 that is disposed over the conductor layer 212, which contains the channels 204 in which the elongate conductors 206 (as best shown in FIG. 11A) are disposed. Further, this specific implementation has three light array sections 214A, 214B, 214C that are physically separated by joints or gaps 216 defined therebetween. Alternatively, there can be two, four, five, six, or any number of separate light array sections in the headgear wall 202, thereby allowing for separate control of each section as described in various embodiments elsewhere herein.

FIG. 11D depicts a different configuration to address the two or more light array sections (such as sections 214A, 214B, 214C as discussed above) in the headgear wall 202. That is, in order to ensure electrical connection between the different sections across the joints/gaps (such as joints/gaps 216 discussed above), a second set of conductors 218A is provided in which the conductors 218A are disposed within the conductor layer 212, rather than disposed within channels on an outer surface of the conductor layer 212. Thus, the configuration has the standard conductors 208 disposed within the channels 204, but it also has the inner conductors 218A disposed within the conductor layer 212 as shown, with electrical connections 218B coupling the standard conductors 208 to the inner conductors 218A. Thus, for each section joint (such as joint 216), an inner (or submerged) conductor 218A is provided such that the conductor 218A can extend along the headgear wall 202 to the central line.

Figure 11E:
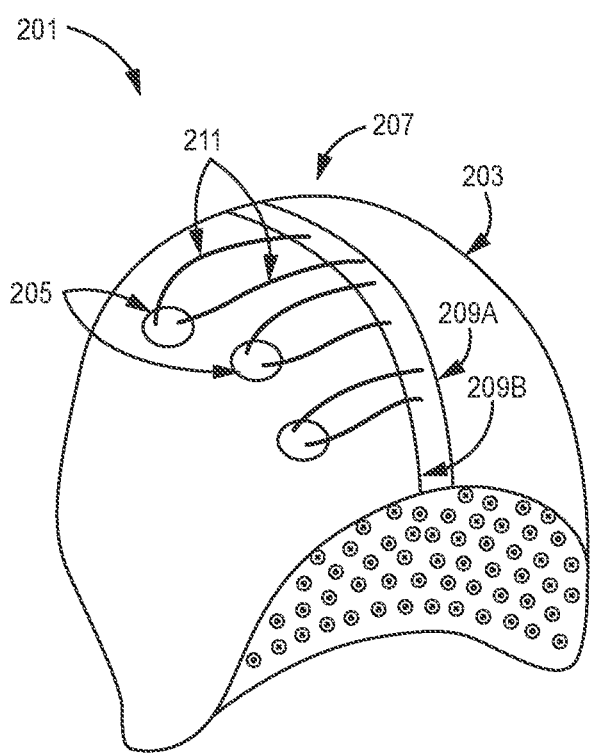
FIG. 11E is a perspective view of a light delivery device with a central power supply and central ground line, according to one embodiment.

In accordance with one implementation, FIG. 11E depicts a light delivery device 201 that is a helmet 203 having three exemplary light assemblies 205 disposed therein, along with an electrical arrangement 207 similar to the arrangement embodiments discussed above. The electrical structure 207 has a central supply line 209A and a central ground line 209B extending along a central portion of the helmet 203. The light assemblies 205 are coupled to the central lines 209A, 209B via the conductive wires 211. In one implementation, the conductive wires 211 are the conductors 206 discussed above. In this implementation, the conductive wires 211 are small gauge and flexible. The central lines 209A, 209B, by comparison, are large gauge and able to carry a larger current, such as for a plurality of light assemblies 205.

Figure 12:
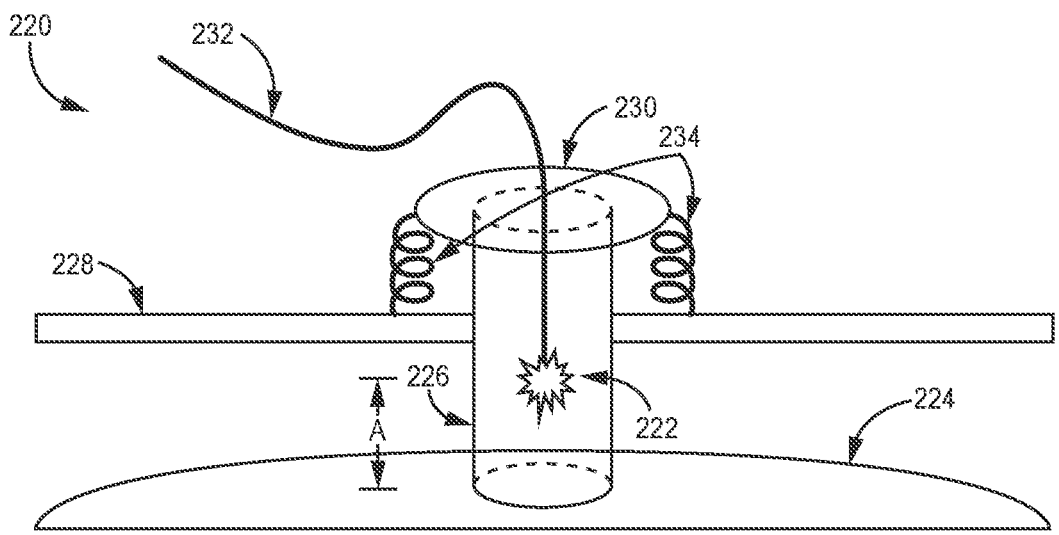
FIG. 12 is a perspective view of a light assembly, according to one embodiment.

FIG. 12 shows one embodiment of a light assembly 220 that can be incorporated into any of the systems or headgear embodiments disclosed or contemplated herein. The assembly 220 maintains at least one light 222 (such as an LED light 222, for example) at a substantially constant distance from the scalp 224 of the patient. The assembly 220 has a tube or other cylindrical structure 226 that is disposed through an opening in the wall 228 of the headgear. The tube 226 has an LED light 222 disposed therein and a plate or cover 230 disposed on the proximal end of the tube 226. The tube 226 is substantially transparent to near infrared light, and the light 222 is positioned at a desired distance A from the bottom of the tube 226. The assembly 220 also has a power supply cable 232 that is coupled to the light 222 and extends out of the tube 226 through an opening in the plate 230. In one embodiment, the cable 232 is attached to plate 230 such that the cable 232 does not move with respect to the plate 230. The cable 232 can be flexible or rigid. Alternatively, the length of the cable 232 within the tube 226 can either be flexible or rigid, while the length of the cable 232 disposed outside of the tube 226 can, independently of the length inside the tube 226, be flexible or rigid.

According to one embodiment, the assembly 220 is tensioned such that it is continuously urged toward the patient's scalp 224 when the assembly 220 is not in contact with the scalp 224. For example, in the specific embodiment of FIG. 12, tension components 234 (which, in this case are springs 234) are coupled to the distal side of the plate 230 and to the outer surface of the wall 228 of the headgear such that the tension components 234 urge the plate 230 (and thus the assembly 220) toward the wall 228. In one embodiment, the tension components 234 compensate for any variations or irregularities in the shape of the patient's skull that result in variations in the distance between the scalp 224 of the patient and the wall 228 of the headgear. According to one embodiment, the force of the tension in the tension components 234 is not so great that the force with which the distal end of the tube 226 is urged against the scalp 224 causes any pain to the patient, but it is sufficiently strong to ensure that the distal end of the tube 226 remains in contact with the scalp 224.

Figure 13:
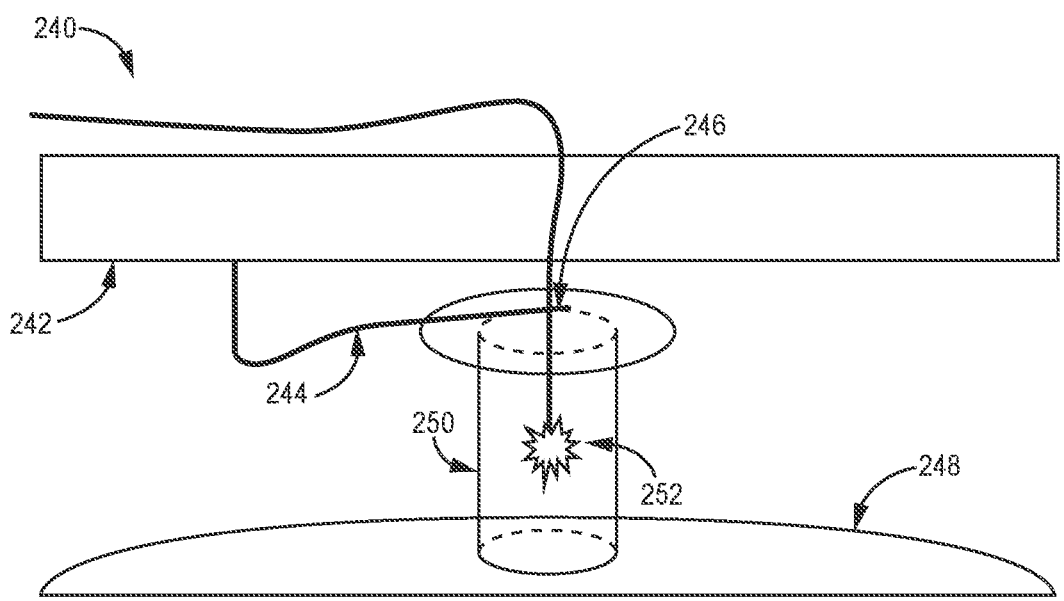
FIG. 13 is a perspective view of a light assembly, according to another embodiment.

FIG. 13 is another embodiment of a light assembly 240 that can be incorporated into any of the systems or headgear embodiments disclosed or contemplated herein. Any of the components or features of this assembly 240 that are not expressly discussed herein are substantially the same as the corresponding components in the assembly 220 embodiment discussed above. In this exemplary implementation, the light assembly 240 is not disposed through the headgear wall 242. Further, this embodiment has a tension component 244 (which, in this case, is a spring lever 244) that is coupled to the plate 246 and to the inner surface of the wall 242 of the headgear such that the tension component 244 urges the plate 246 (and thus the assembly 240) toward the patient's scalp 248. In one embodiment, like the previous embodiment of FIG. 12, the tension component 244 compensates for any variations or irregularities in the shape of the patient's skull that result in variations in the distance between the scalp 248 of the patient and the wall 242 of the headgear. According to one embodiment, like the previous embodiment, the force of the tension in the tension component 244 is not so great that the force with which the distal end of the tube 250 is urged against the scalp 248 causes any pain to the patient, but it is sufficiently strong to ensure that the distal end of the tube 250 remains in contact with the scalp 248, thereby ensuring that the light 252 is disposed at a predetermined distance from the scalp 248.

Figure 14:
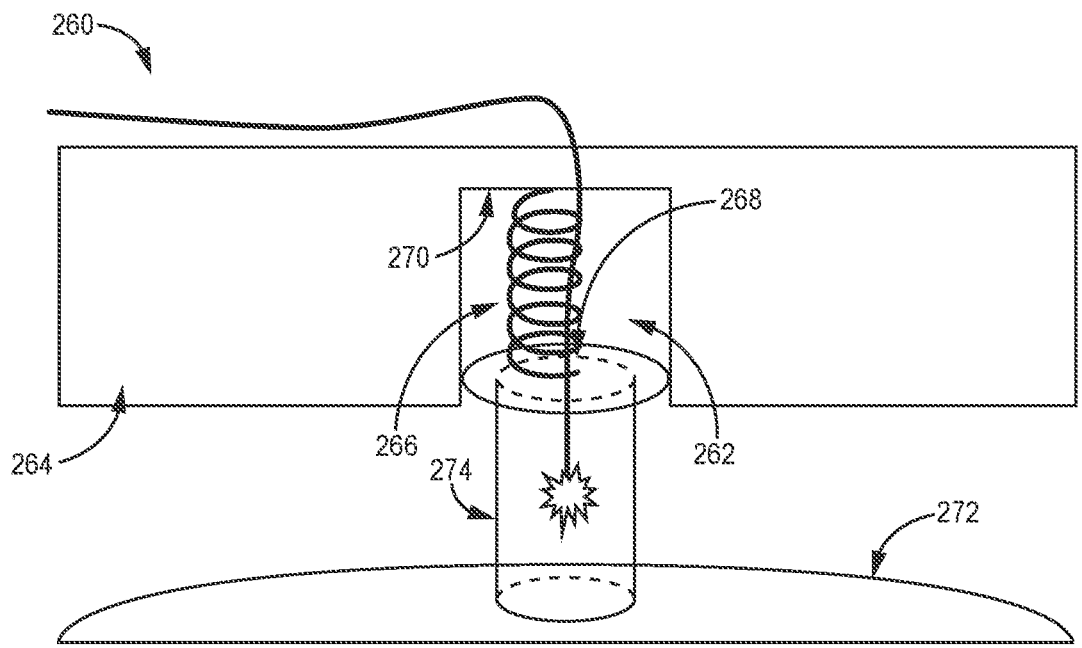
FIG. 14 is a perspective view of a light assembly, according to a further embodiment.

FIG. 14 depicts another embodiment of a light assembly 260 that can be incorporated into any of the systems or headgear embodiments disclosed or contemplated herein. Any of the components or features of this assembly 260 that are not expressly discussed herein are substantially the same as the corresponding components in the assembly 220, 240 embodiments discussed above. In this exemplary implementation, a portion of the light assembly 260 is disposed within an opening or cavity 262 defined or otherwise formed in the headgear wall 264 as shown. Further, this embodiment has a tension component 266 (which, in this case, is a tension spring 266) that is coupled to the plate 268 and to the inner surface 270 of the opening 262 of the headgear such that the tension component 266 urges the plate 268 (and thus the assembly 260) toward the patient's scalp 272. In one embodiment, like the previous embodiment, the tension component 266 compensates for any variations or irregularities in the shape of the patient's skull that result in variations in the distance between the scalp 272 of the patient and the wall 264 of the headgear. According to one embodiment, like the previous embodiments, the force of the tension in the tension component 266 is not so great that the force with which the distal end of the tube 274 is urged against the scalp 272 causes any pain to the patient, but it is sufficiently strong to ensure that the distal end of the tube 274 remains in contact with the scalp 272.

Figure 15:
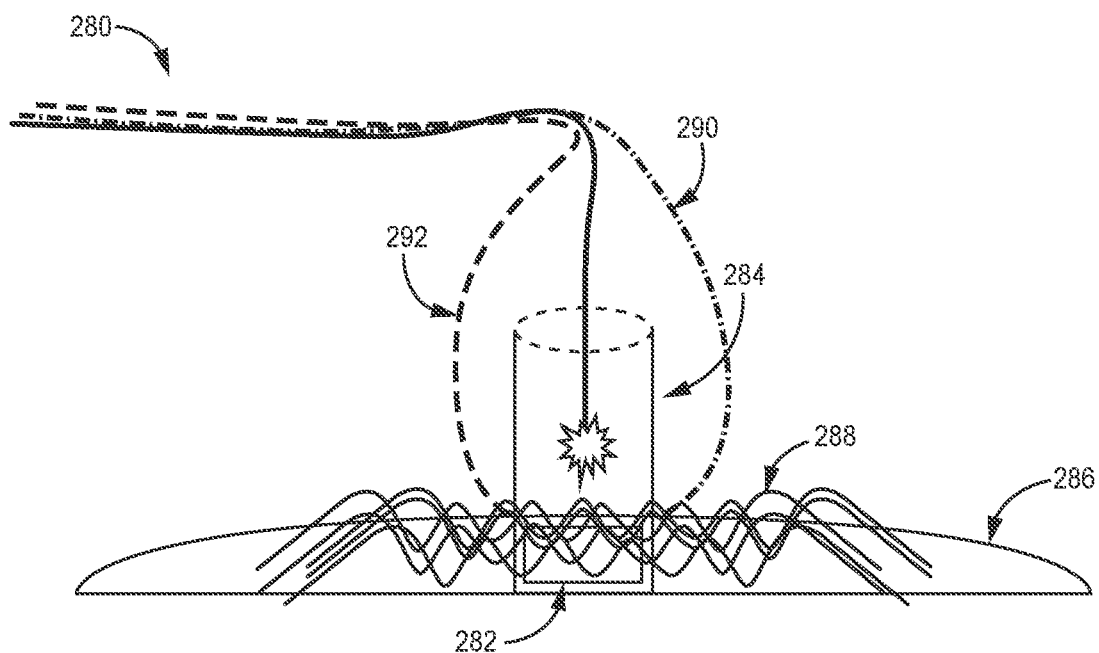
FIG. 15 is a perspective view of a light assembly, according to yet another embodiment.

FIG. 15 shows a further embodiment of an LED assembly 280 according to any of the assembly embodiments disclosed or contemplated herein and its use with a light measurement device (in this case, a spectrometer) 282 within the headgear that can be incorporated into any of the systems or headgear embodiments disclosed or contemplated herein. Any of the components or features of this assembly 280 that are not expressly discussed herein are substantially the same as the corresponding components in the assembly 220, 240, 260 embodiments discussed above. While the plate attached to the top of the tube 284 and the tension component (which can be any of the tension component embodiments disclosed or contemplated herein) are not shown, it is understood that any plate and/or tension component as disclosed or contemplated herein with respect to any other light assembly embodiment can be incorporated herein. In this embodiment, the spectrometer 282 is disposed at the distal end of the assembly 280 and is positioned against the patient's scalp 286 underneath the patient's hair 288. In one embodiment, the spectrometer 282 is powered by a power supply cable 290, and the output of the spectrometer 282 is transmitted to a human-readable processor or a microprocessor or any known controller by data transmission cable 292. According to certain embodiments, an array of these light assemblies 280 can be incorporated into the system 299 of FIG. 2, which specifically contemplates the use of a spectrometer 40 within the light delivery device 32 as discussed in detail above.

Figure 16:
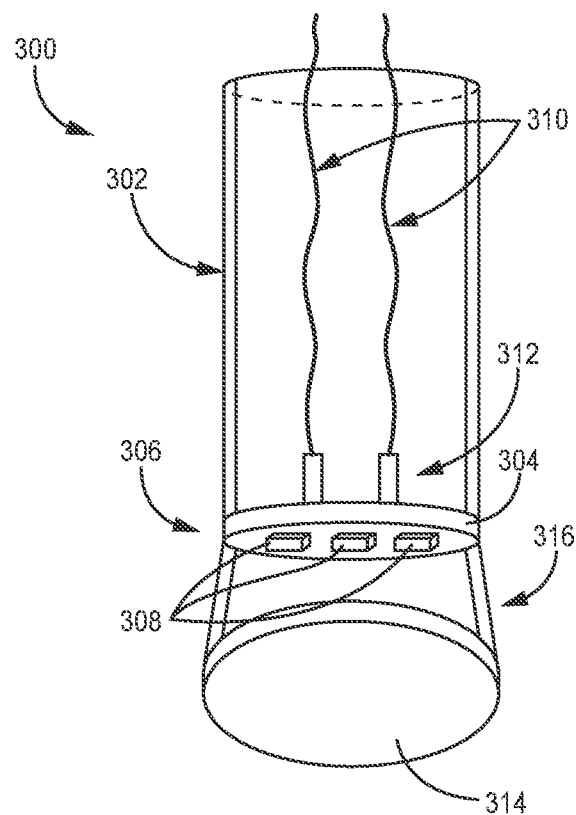
FIG. 16 is a perspective view of a light assembly, according to yet a further embodiment.

Alternatively, instead of the light assembly embodiments as depicted in FIGS. 12-15 in which the lights are disposed inside of cylindrical structures ("through-hole light assemblies"), other implementations relate to light assemblies having one or more LED lights mounted on a surface of a printed circuit board. One such example is depicted in FIG. 16, in which the light assembly 300 has a cylindrical or tubular structure 302, a printed circuit board ("PCB") 304 disposed at the distal end 306 of the structure 302, LED lights 308 disposed on the distal surface of the PCB 304, and power supply (and ground) cables 310 coupled to connectors 312 that are coupled to the PCB 304. In one embodiment, the assembly 300 can also have a lens 314 as shown that is coupled to the distal end 306 of the structure 302 such that the lens 314 is disposed between the lights 308 and the scalp of the patient (not shown).

In this specific exemplary embodiment as shown, the light assembly 300 has three LED lights 308. Alternatively, the number of LED lights 308 on the PCB 304 can range from one to eight LED lights 308. In a further alternative, the PCB 304 can have any number of LED lights 308. The LED lights 308 can be any known LED lights 308. In certain implementations, at least one of the LED lights 308 on the PCB 304 can emit light of one wavelength, while at least one other LED light 308 can emit light of another wavelength. Alternatively, all of the lights 308 on the PCB 304 emit light of the same wavelength. In accordance with certain embodiments, the LED lights 308 are coupled to the PCB 304 via surface mount pads. Alternatively, the lights 308 can be coupled to the PCB 304 in any known fashion using any known mechanism or method. It is understood that the resistors (not shown) that are coupled to and control the voltage and current to the LED lights 308 are also mounted on the PCB 304 and also that the traces (not shown) that couple the power supply cables 310 to the LED lights 308 are built into the PCB 304.

In various implementations, the PCB-mounted LED light assembly 300 has a lower profile in comparison to any of the through-hole light assemblies described above. That is, the lights 308 mounted on the distal end of the cylindrical structure 302 allows for the overall length of the cylindrical structure 302 to be less than the length of the cylindrical structures of the through-hole light assemblies as discussed in detail above. As such, the PCT-mounted LED light assembly embodiments disclosed or contemplated herein (such as the assembly 300) allow for a lower profile structure that can result in the wall of the light delivery device in which the light assemblies 300 are disposed being thinner or requiring less thickness in comparison to any light delivery device containing through-hole light assemblies.

In various embodiments, an array of the PCB-mounted LED light assemblies (such as assembly 300) will be provided in any of the light delivery device embodiments disclosed or contemplated herein. In certain implementations, the plurality of light assemblies on one light delivery device can include light assemblies of different sizes such that the PCB boards are of different sizes. As such, some of the light assemblies will have larger PCB boards that contain more LED lights (like a PCB board containing eight LED lights, for example), while some of the light assemblies will have smaller PCB boards that contain few LED lights (like a PCB board containing two LED lights). Alternatively, the PCB 304 on the light assembly 300 can be a multi-layer board that is segmented into multiple pieces such that the various pieces are somewhat flexible in relation to each other, thereby providing for a PCB 304 that is conformable to or flexible in relation to the patient's head. The mix of light assemblies of different sizes in the light delivery device and/or the flexibility of the PCBs therein will provide for an inner surface of the light delivery device having either many smaller PCBs or a mix of PCBs of varied sizes such that the resulting configuration will fit around the patient's head more easily than can be accomplished with a smaller number of larger PCBs.

Figure 18:
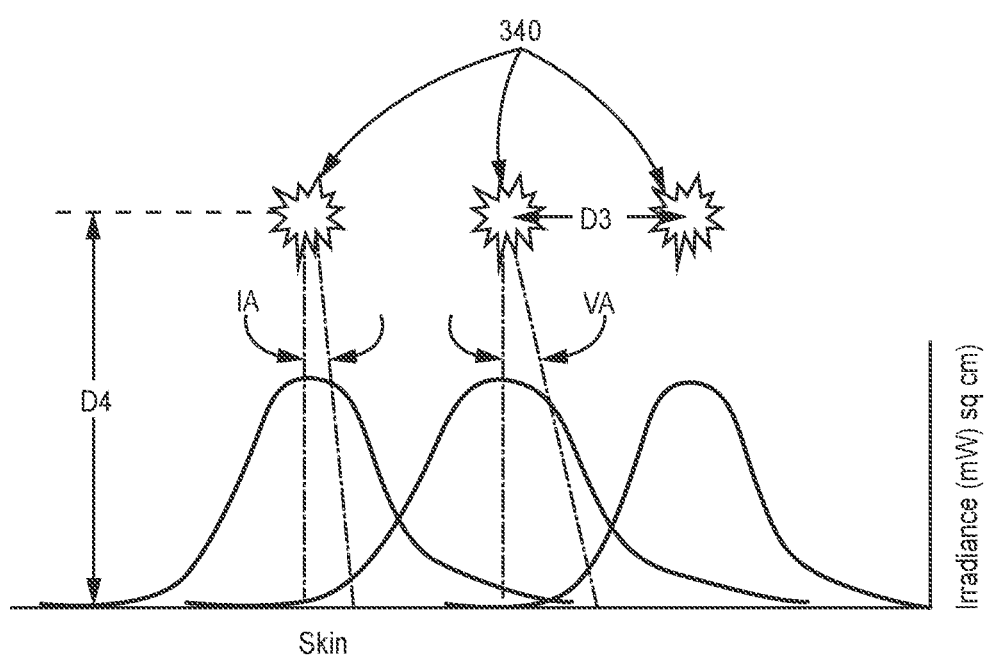
FIG. 18 is a schematic depiction of three light assemblies and certain light characteristics thereof, according to another embodiment.

As mentioned above, the light assembly 300 in FIG. 16, according to one embodiment, has a lens 314 incorporated therein. Any of the components or features of this assembly 300 that are not expressly discussed herein are substantially the same as the corresponding components in the assembly 220, 240, 260, 280 embodiments discussed above. It is understood that any of the other light assembly embodiments disclosed or contemplated herein, including light assemblies 220, 240, 260, 280 as discussed above, can have a lens (such as lens 314) incorporated therein. The lens 314 is coupled via a sleeve 316 to the distal end 306 of the cylindrical structure 302. In one embodiment, the sleeve 316 is transparent, thereby allowing light from the LED lights 308 to pass therethrough. Alternatively, any structure, such as arms or any such attachment components, can be incorporated into the assembly 300 to couple the lens 314 to the cylindrical structure 302. The lens 314 can help to reduce "hot spots" or uneven distribution of light intensity on the patient's scalp by "evening out" or "smoothing" the application of light across the scalp surface. That is, many lights, including, for example, LEDs, have a relatively small "view angle," which is the angle from the center of the light at which the intensity of emitted light drops to half its maximal intensity. One example of the view angle (v) is depicted in FIG. 18, as discussed below. The result of this small view angle is that the lights of the light assemblies must be positioned relatively close together (in comparison to lights with larger view angles) in order to assure thorough and even application of the light on the patient's scalp. However, the close proximity of the lights can result in "hot spots" of increased intensity on the irradiated surface. The lens 314 is mounted or otherwise disposed between the light and the irradiated surface (scalp) such that the lens can even out the application of the light, thereby minimizing hotspots and improving the overall evenness of the light distribution across the scalp. In one embodiment, the lens 314 can be a concave lens or a Fresnel lens. Alternatively, the lens 314 can be any known lens that can help to smooth out light distribution.

In those system/device implementations discussed herein that incorporate a light measurement device, the device can be used to monitor energy delivery at the scalp of the patient (including, for example, through thick hair) to ensure the power generated by the light assemblies is sufficient to ensure adequate irradiance at the cortex. While the various specific embodiments discussed herein include a spectrometer, it is understood that any of these embodiments can have any type of light measurement device, including, for example, a photometer, a luminance meter, an illuminance meter, a spectroradiometer, or a light meter. In addition, according to further embodiments, any of the various system and device embodiments herein can also include feedback-controlled software that functions in conjunction with the light measurement device to monitor the irradiance delivered to the patient's scalp (including, in various embodiments, through the patient's hair) and provide feedback control to ensure sufficient therapeutic fluence is delivered. According to one implementation, the control software runs a control loop by using the light measurement device positioned at the scalp to calculate the fluence for a predetermined period of time. The light measurement device can be placed anywhere along the patient's scalp such that it is between the scalp and the light assembly (or light assemblies). In certain embodiments in which the goal is to adjust the applied fluence to address the patient's hair thickness, the light measurement device is placed specifically in the area of the patient's scalp where the hair is thickest. In accordance with one implementation, the predetermined period of time can range from about a millisecond to about 15 minutes. Alternatively, the period of time can range from about a millisecond to about 10 minutes. In a further implementation, the period of time is a millisecond. In yet another alternative, the predetermined period of time is any relatively short period of time that does not disrupt the method of use as described herein.

In use, according to one embodiment, any system disclosed or contemplated herein having the feedback control software can operate in the following fashion. First, the light measurement device is placed in the desired location, and the location on the patient's scalp is entered into the software. Next, the control software is actuated to trigger one or more predetermined light assemblies to radiate light for the predetermined period of time such that the light measurement device collects information about the fluence and transmits that information to the software. The software compares the collected fluence data to the reference (or calibrated) value for fluence (such as the reference fluence for no hair) and calculates the appropriate level of applied fluence to achieve the desired level of therapeutic fluence. At this point, the light measurement device is removed, and the software provides adjusted actuation to the one or more light assemblies to radiate light at the adjusted applied fluence, thereby resulting in the desired applied fluence that generates the desired therapeutic fluence. In certain implementations, the software would also take into account the amount of fluence applied during the measurement period and adjust the timing and/or power of the therapy cycle accordingly.

Figure 17:
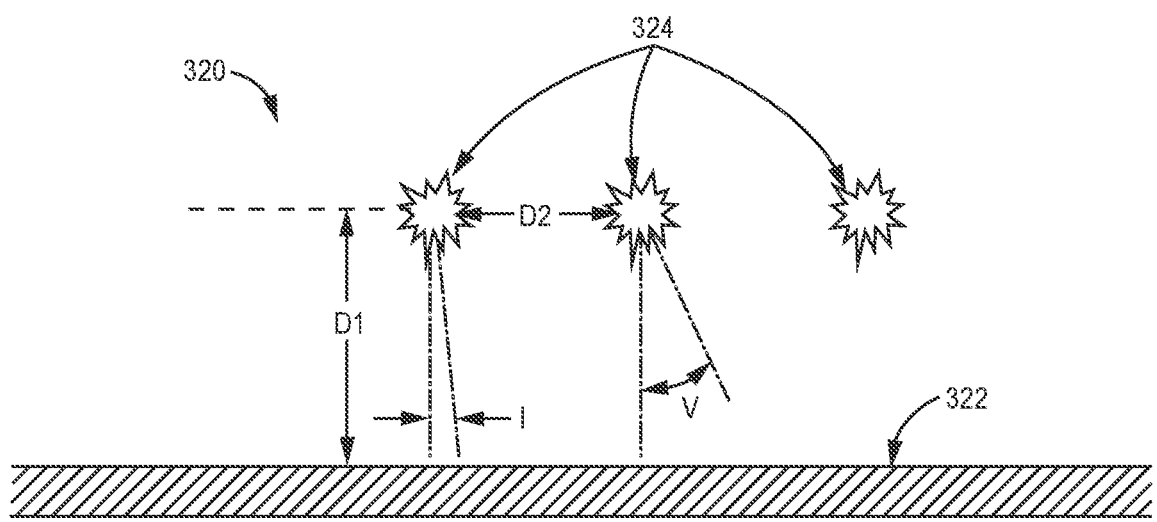
FIG. 17 is a schematic depiction of three light assemblies and certain light characteristics thereof, according to one embodiment.

FIG. 17 depicts, according to one embodiment, the relative position of multiple assemblies of at least one light 320 with respect to each other, and with respect to the wearer's scalp 322. The lights 324 of a characteristic radiant intensity R also have a characteristic viewing angle V when viewed from directly below the light source 324 when it is pointed directly down. The viewing angle V is the angle from directly below the light 324 at which the irradiance drops to 50% of its peak value. The lights 324 are positioned a distance x D1 from the scalp 322 and a distance d D2 apart from each other. The incident angle a I is the angle from directly axial below the LED from which the LED is viewed. The irradiance on the patient's scalp 322 resulting from the lights when pointed toward the scalp 322 may be characterized according to the following equation 1:

$$\text{Irradiance}, I = \frac{R}{1+x^2} \cos\frac{a}{v} \quad (1)$$

where a, v, R and x are described previously. As can be seen from FIG. 18, the resultant irradiance from a light 324 varies on the scalp 322 with position and angle with respect to the light 324. An examination of equation 1 will make it clear there are many different combinations of characteristic LED light radiant intensity, separation from the scalp and viewing angle that can be used to obtain a desired irradiance at the skin. Table 1 has examples of such combinations, all at incidence angle a set to zero, thus applicable to any viewing angle.

TABLE 1

| Irradiance, I (mW/sq cm) | Radiant Intensity, R (mW) | Separation from skin, x (cm) |
|---|---|---|
| 15 | 15 | 1.000 |
| 15 | 30 | 1.414 |
| 15 | 7.5 | 0.707 |
| 30 | 30 | 1.000 |
| 30 | 60 | 1.414 |
| 30 | 15 | 0.707 |

The relative position of the light assemblies with respect to each other are determined by the characteristic viewing angle of the lights. The relationship of the separation d between light assemblies to the viewing angle of the light is shown in equation 2.

$$d = 2x \tan v \quad (2)$$

It is again clear upon examination that there are many different combinations of viewing angle v and LED/scalp separation x that can be used to obtain a desired separation between the light assemblies. Examples of various combinations are shown in Table 2.

TABLE 2

| Separation between LEDs, d (cm) | Separation from skin, x (cm) | Viewing Angle, v (radians) |
|---|---|---|
| 2.00 | 1.000 | 0.785 |
| 2.00 | 1.414 | 0.615 |
| 2.00 | 0.707 | 0.955 |
| 3.00 | 0.500 | 1.249 |
| 3.00 | 0.250 | 1.406 |
| 3.00 | 2.000 | 0.643 |

Depicted in FIG. 18 is a graphic representation of irradiance at the patient's scalp from lights of radiant intensity R 340 for a given combination of parameters separated from each other by distance d D3 and separated from the scalp by a distance x D4 and with characteristic viewing angle v VA of the light. Also shown is the variation in the irradiance at the scalp with respect to incident angle a IA across a distance of the scalp.

In certain implementations, the various systems and/or devices disclosed or contemplated herein can include integrated safety features to prevent misuse and/or injury. For example, in one embodiment, any system embodiment herein can have control software or hardware components that prevent use of the system/device for longer than a maximum use time that is set by a healthcare provider. For example, the maximum use time in one embodiment can be one hour. Alternatively, the control software or hardware components can prevent use of the system/device more than a maximum number of uses over a predetermined period of time. For example, the maximum number of uses can be two uses over 48 hours. In a further alternative, the control software or hardware components can provide both a maximum use time and a maximum number of uses over a predetermined period of time.

According to one exemplary embodiment, the system controller can have a counter/timer that would track the amount of time that the patient is exposed to the therapeutic energy such that the controller can shut down the light arrays when the maximum time period has been reached. Further, the controller can also track the number of uses over any predetermined time period and can prevent activation of the light arrays for the remainder of the time period after the maximum number of allowed uses has been reached. It is understood that the various parameters for these safety control features can be inputted by the physician or other healthcare provider prior to use by the patient. That is, the appropriate limits can be decided by the physician, and then the physician or other healthcare provider can input those limits into the system via the interface. In certain implementations, the controller would also provide a locking mechanism, such as a passcode or other such mechanism, to prevent the patient from adjusting the safety features.

It is understood that the various system embodiments having the safety features as described in detail above will have to have uninterrupted power even when the system is not in use such that the controller can continue to track passage of time and the usage of the system as described above. In one embodiment, the power source can be a battery or alternatively can be electricity delivered from an outlet. In a further implementation, the power source can be any known power source that provides uninterrupted power.

In accordance with certain specific implementations, the various systems herein can also have a communication component. That is, the controller in the system can be coupled to a communication transmission mechanism such that the controller can transmit messages to a phone, a computer, or any other type of communication device via text message, e-mail, or any other form of communication. Alternatively, the communication can be an alert that is provided by the system or device itself in the form of a visual or audible alert. In one embodiment, the controller can transmit messages or alerts to the patient to notify the patient that the use of the system has exceeded the safety limitations in period of use, number of uses, or some other parameter. According to a further embodiment, the controller can transmit messages or alerts to a healthcare provider notifying the provider that the safety parameters have been exceeded. In a further embodiment, the controller can transmit messages or alerts to the patient to remind the patient (or to the healthcare provider) that it is time to use the system again.

In use, according to one embodiment, a patient can use the system and have energy applied to the patient's skull for the first prescribed time period at the prescribed applied fluence levels. When the patient next attempts to use the system for her next therapy, the controller compares the current date and time to the date and time of the prior therapy. If the elapsed period is equal to or greater than the predetermined time period, the controller will activate the power to the light assemblies. On the other hand, if the elapsed period is less than the predetermined safety time period, the controller will not allow activation of the light assemblies.

In an alternative embodiment in which the system is used in a group setting, such as a clinic or hospital, for example, the same system may be used by multiple patients. As such, safety control mechanisms can be incorporated into the system that are configured to address the usage by more than one patient. More specifically, the system will have software associated with the controller that requires each patient that uses the system to have a unique identifier that must be provided to the controller by some mechanism. In one embodiment, the unique identifier can be a password, a barcode, a keyfob, or any other known unique identifier that can be used such that the system can identify each individual patient. As such, it is understood that the system can have any type of input mechanism to allow for input of that unique identifier depending on the type of identifier. After entry of the unique identifier, the controller operates in a fashion similar to that described above for general operation, except that the parameters and tracking information are patient specific. That is, the control software tracks and stores the date and time of use indexed for each patient and then compares the date and time of Patient A's current use to the date and time of Patient A's prior use. As in general operation, if the elapsed time since Patient A's prior use is less than the predetermined period, the controller will not activate the system, etc.

Although the present invention has been described with reference to preferred embodiments, persons skilled in the art will recognize that changes may be made in form and detail without departing from the spirit and scope of the invention.

What is claimed is:

1. A traumatic brain injury treatment system, comprising:
    (a) a headpiece comprising:
        (i) a housing comprising:
            1) a head cavity defined by the housing; and
            2) an inner surface within the head cavity; and
        (ii) a light array disposed on the inner surface, wherein the light array comprises a plurality of LED light assemblies, wherein the plurality of LED light assemblies further comprise a portion of the LED light assemblies disposed adjacent to a front sinus or a mastoid process of a patient's head when the patient's head is disposed within the housing, wherein the portion of the LED light assemblies disposed adjacent to the front sinus or the mastoid process have a different radiant intensity or are actuated to radiate for a different period of time than other LED light assemblies in the plurality of LED light assemblies;
    (b) a power/communication line coupled to the light array;
    (c) a controller coupled to the power/communication line; and
    (c) an energy source coupled to the power/communication line.

2. The traumatic brain injury treatment system of claim 1, wherein each of the plurality of LED light assemblies comprises:
    (a) a substantially transparent tubular structure;
    (b) an LED light disposed at a fixed longitudinal position with the tubular structure; and
    (c) a tension component coupled to the tubular structure and the inner surface of the housing.

3. The traumatic brain injury treatment system of claim 2, wherein each of the plurality of LED light assemblies further comprises a cover disposed on a proximal end of the tubular structure, wherein the tension component is coupled to the tubular structure at the cover.

4. The traumatic brain injury treatment system of claim 2, wherein the tension component comprises at least one spring or a lever.

5. The traumatic brain injury treatment system of claim 2, wherein the tubular structure is disposed through an opening in the inner surface of the housing.

6. The traumatic brain injury treatment system of claim 2, wherein the tubular structure is disposed adjacent to and tensionably coupled to the inner surface.

7. The traumatic brain injury treatment system of claim 2, wherein the tubular structure is disposed at least partially within a cavity defined within the inner surface.

8. The traumatic brain injury treatment system of claim 1, wherein the housing further comprises two movable side panels hingedly coupled to the housing, wherein the two movable side panels comprise a closed position and an open position.

9. The traumatic brain injury treatment system of claim 1, wherein the housing further comprises a movable rear panel hingedly coupled to the housing, wherein the movable rear panel comprises a closed position and an open position.

10. The traumatic brain injury treatment system of claim 1, wherein the housing comprises a substantially flexible material.

11. The traumatic brain injury treatment system of claim 1, wherein the housing comprises a substantially rigid material.

12. The traumatic brain injury treatment system of claim 1, wherein the housing further comprises a visor disposed on a front portion of the housing.

13. The traumatic brain injury treatment system of claim 1, wherein the housing further comprises two ear coverings, wherein each of the two ear coverings is disposed on a side of the housing.

14. The traumatic brain injury treatment system of claim 1, wherein the different radiant intensity is greater radiant intensity ranging from about 15% to about 50% greater intensity than the other LED light assemblies in the plurality of LED light assemblies.

15. The traumatic brain injury treatment system of claim 1, wherein the different radiant intensity is greater radiant intensity resulting from a more powerful LED light or a shorter distance between an LED light and an irradiated surface of the patient's head.

16. The traumatic brain injury treatment system of claim 1, wherein the plurality of LED light assemblies further comprise a portion of the LED light assemblies disposed adjacent to a sphenoid bone of a patient's head when the patient's head is disposed within the housing, wherein the portion of the LED light assemblies disposed adjacent to the sphenoid bone have a different radiant intensity than other LED light assemblies in the plurality of LED light assemblies.

17. The traumatic brain injury treatment system of claim 16, wherein the different radiant intensity is lesser radiant intensity resulting from a less powerful LED light or a greater distance between an LED light and an irradiated surface of the patient's head.

18. The traumatic brain injury treatment system of claim 1, wherein specific portions of the plurality of LED light assemblies have predetermined, differing radiant intensities depending on a position of the specific portions within the housing.

19. The traumatic brain injury treatment system of claim 1, further comprising a protective cap having a low absorbance of near infrared wavelengths, wherein the protective cap is positionable on a patient's head such that the protective cap is disposed between the patient's head and the inner surface of the housing.

20. The traumatic brain injury treatment system of claim 1, wherein each of the plurality of LED light assemblies comprises:
   (a) a substantially transparent tubular structure; and
   (b) an LED light disposed at a fixed longitudinal position with the tubular structure.

21. A traumatic brain injury treatment system, comprising:
   (a) a headpiece comprising:
      (i) a housing comprising:
         1) a head cavity defined by the housing;
         2) An inner surface within the head cavity; and
         3) an electrical arrangement comprising:
            (A) a central supply line disposed along a central location within the housing;
            (B) a central ground line disposed adjacent to the central supply line; and
            (C) a conductor layer disposed within the housing, the conductor layer comprising:
               (I) at least two channels defined within the conductor layer; and
               (II) at least two conductors, wherein each of the at least two conductors is disposed within a separate one of the at least two channels, wherein the at least two conductors are coupled at a first end to the central supply line or the central ground line and further are coupled at a second end to at least one of the plurality of LED light assemblies; and
      (ii) a light array disposed on the inner surface, wherein the light array comprises a plurality of LED light assemblies;
   (b) a power/communication line coupled to the light array;
   (c) a controller coupled to the power/communication line; and
   (d) an energy source coupled to the power/communication line.

22. The traumatic brain injury treatment system of claim 21, wherein the housing comprises at least two light array sections.

23. The traumatic brain injury treatment system of claim 2, further comprising a lens coupled to a distal end of the tubular structure.

24. The traumatic brain injury treatment system of claim 23, wherein the lens is coupled to the distal end of the tubular structure via a sleeve.

25. The traumatic brain injury treatment system of claim 1, wherein the controller comprises a safety module, wherein the safety module has a maximum use time or a maximum use count, wherein the controller is configured to prevent actuation of any of the plurality of LED light assemblies when the maximum use time or the maximum use count has been exceeded.

26. The traumatic brain injury treatment system of claim 21, wherein the plurality of LED light assemblies comprises at least two light assembly sections, wherein each of the at least two light assembly sections are configured to generate different radiant intensities.

27. The traumatic brain injury treatment system of claim 26, wherein each of the at least two light assembly sections are actuable to generate different radiant intensities by radiating for a different period of time in comparison to another of the at least two light assembly sections.

28. A method of treating a traumatic brain injury, the method comprising:
   positioning a treatment system for treatment of a patient, the treatment system comprising:
      (a) a headpiece comprising:
         (i) a housing comprising:
            1) a head cavity defined by the housing; and
            2) an inner surface within the head cavity;
         (ii) a light array disposed on the inner surface, wherein the light array comprises a plurality of LED light assemblies;
      (b) a power/communication line coupled to the light array;
      (c) a controller coupled to the power/communication line;
      (d) an energy source coupled to the power/communication line; and
      (e) a light measurement device coupled to the controller, wherein the light measurement device is disposed adjacent to at least one of the plurality of LED light assemblies,
      wherein the positioning the treatment system comprises positioning the headpiece on the patient's head with the light measurement device on the patient's scalp;
   actuating at least one of the plurality of LED light assemblies to radiate light toward the patient's scalp;
   receiving at least a portion of the radiated light at the light measurement device;

transmitting information about the at least a portion of the radiated light from the light measurement device to the controller;

calculating an appropriate level of applied fluence at the controller based on the information about the at least a portion of the radiated light; and actuating the at least one of the plurality of LED light assemblies to radiate light at the appropriate level of applied fluence.

\* \* \* \* \*